United States Patent
Aoki et al.

[11] Patent Number: 6,088,096
[45] Date of Patent: Jul. 11, 2000

[54] END-POINT DETECTOR FOR PLASMA ETCHER

[75] Inventors: Masahiro Aoki, Tokyo; Susumu Saito, Kofu, both of Japan

[73] Assignee: Tokyo Electron Limited, Tokyo, Japan

[21] Appl. No.: 09/096,524

[22] Filed: Jun. 12, 1998

[30] Foreign Application Priority Data

Jun. 20, 1997 [JP] Japan ................................. 9-164191

[51] Int. Cl.$^7$ ................................................. G01J 3/04
[52] U.S. Cl. ............................. 356/316; 356/310; 356/303
[58] Field of Search .................................. 356/300, 316, 356/310, 302, 303

[56] References Cited

U.S. PATENT DOCUMENTS

| | | | |
|---|---|---|---|
| 5,626,714 | 5/1997 | Miyazaki et al. | 356/316 |
| 5,728,253 | 3/1998 | Saito et al. | 356/316 |

FOREIGN PATENT DOCUMENTS

| | | |
|---|---|---|
| 5-62943 | 3/1993 | Japan . |
| 7-321094 | 12/1995 | Japan . |

*Primary Examiner*—Robert H. Kim
*Assistant Examiner*—Reginald A. Ratliff
*Attorney, Agent, or Firm*—Oblon, Spivak McClelland, Maier & Neustadt, P.C.

[57] ABSTRACT

An end-point detector for a plasma etcher, includes a converging lens for receiving strip-like plasma light produced between a pair of opposed electrodes and a spectroscope, having a slit located at a substantial rear-side focal plane of the converging lens, for detecting an etching end time point from a time-based variation of spectrum light intensity of the plasma light which has been converged at the slit and has passed through the slit. The converging lens has a pupil diameter of not greater than $$\phi = \frac{W + \sqrt{W^2 - 8hlNA_m}}{2}$$

where W is a width of a short side of the strip-like plasma light produced between the electrodes, 1 is a distance between an end of each electrode and a pupil face of the converging lens, NAm is a numerical aperture required by the spectroscope, and h is a width of a short side of the slit of the spectroscope. The converging lens has a numerical aperture of not less than NAm.

7 Claims, 6 Drawing Sheets

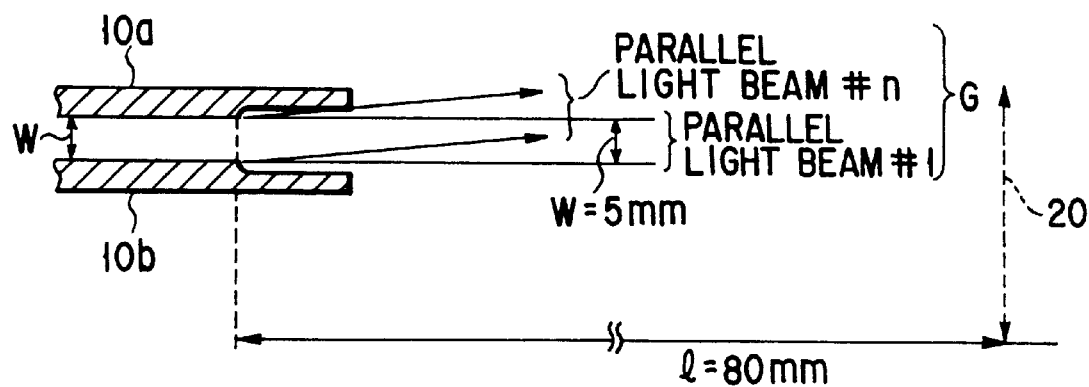
F I G. 2
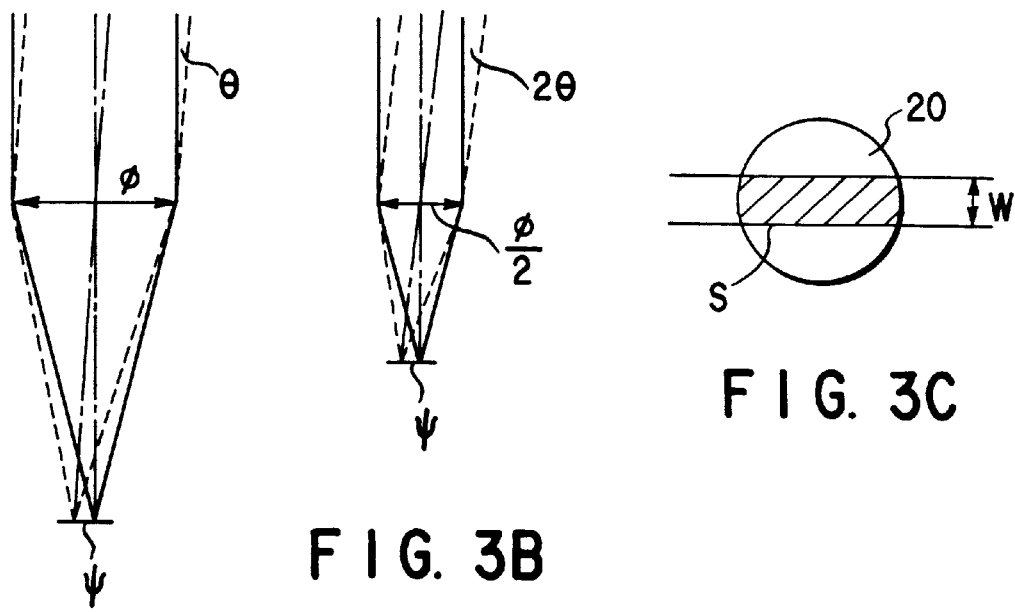
F I G. 3A  F I G. 3B  F I G. 3C

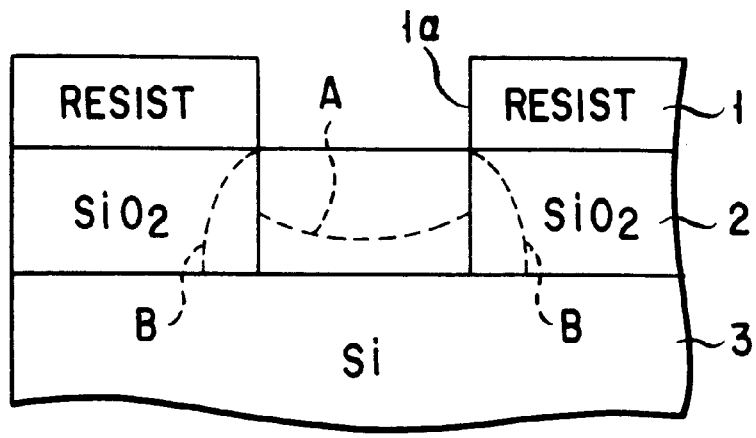
F I G. 8
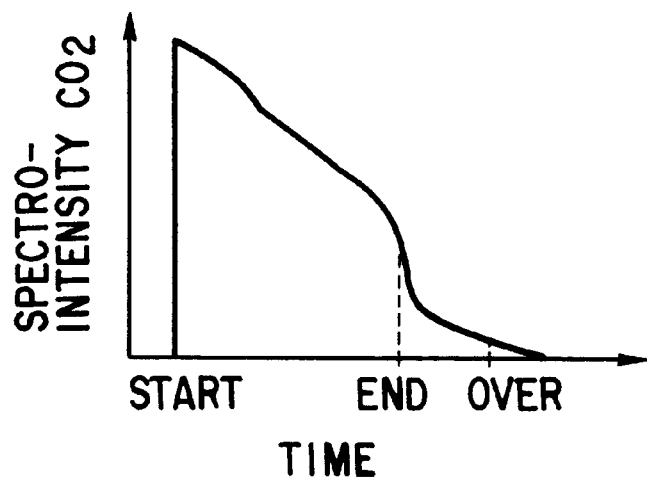
F I G. 9

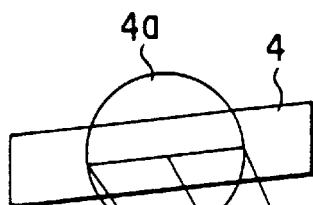
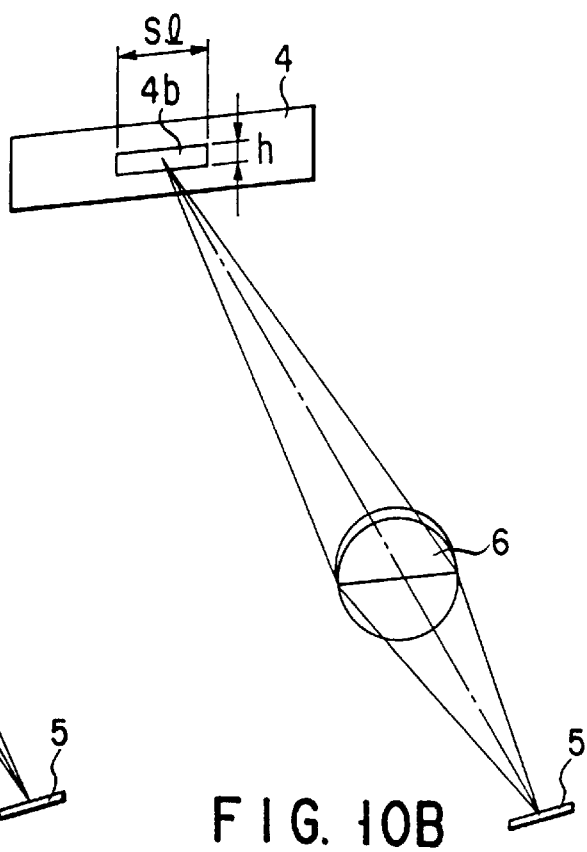
FIG. 10A
RELATED ART
FIG. 10B
RELATED ART
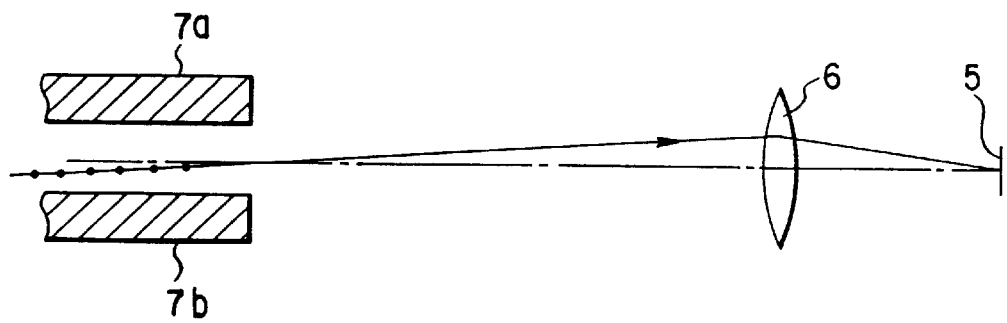
FIG. 11
RELATED ART

END-POINT DETECTOR FOR PLASMA ETCHER

BACKGROUND OF THE INVENTION

The present invention relates to an end-point detector for a plasma etcher, which spectrometrically measures plasma light produced in a plasma etching (dry etching) step in a semiconductor-device manufacturing process, detects a time-based variation of measured spectrum intensity, and controls an etching end time point.

In general, in a plasma etcher, a reaction or process gas is introduced into a chamber and a radio-frequency voltage is applied between an upper electrode and a lower electrode serving also as a susceptor within the chamber at a predetermined distance therebetween. Thereby, a plasma of a process gas is produced between both electrodes and a fine pattern is formed by etching a semiconductor wafer or a film formed thereon placed on the susceptor.

Precise end-point detection by the plasma etcher is presently required, for example, in a step of etching an $SiO_2$ film for formation of a contact hole or holes.

In the step of etching the $SiO_2$ film, as shown in FIG. 8, an Si wafer 3, on which an $SiO_2$ film 2 covered with a resist 1 having an opening 1a with a predetermined pattern is provided, is set on a susceptor. Then, while a mixture gas of $CF_4$ and Ar is supplied as a process gas into the chamber, a radio-frequency voltage is applied between the electrodes. As a result, the following reaction occurs on an exposed portion of the $SiO_2$ film through the opening 1a:

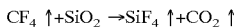

$$CF_4 \uparrow + SiO_2 \rightarrow SiF_4 \uparrow + CO_2 \uparrow$$

Thus, $SiO_2$ is etched.

In this case, there is a problem in the control of reaction time. If the reaction time is too short, the exposed portion of the $SiO_2$ film is not completely removed and is left, as indicated by a broken line A. If the reaction time is too long, etching progresses deep into the region of $SiO_2$ film which is covered with the resist, as indicated by a broken line B. This state is so-called "over-etching". Such defects in etching will seriously degrade the quality of products.

In the prior art, in order to solve the above problems, there is known a method of monitoring a spectrum intensity of a gas produced by the reaction of $SiO_2$ ($CO_2$ gas in this case), thereby controlling the reaction time. The spectrum intensity of $CO_2$ gas varies with the passing of the reaction time, as shown in FIG. 9 by a solid line. The time of variation in spectrum intensity of $CO_2$ gas in this case comprises a time period in which the intensity gradually decreases from the beginning of etching with progression of etching, a time period in which the intensity sharply decreases near an end point of etching, and a time period in which the intensity gradually until the occurrence of over-etching state. Accordingly, if the reaction time is controlled at around the time point at which the spectrum intensity sharply varies, the optimal etching state is attained. In the prior art, plasma light within the chamber is thus measured by the spectrometer and the spectrum intensity of $CO_2$ gas is measured by a photodetector, and the reaction time is controlled at around the time point at which the spectrum intensity sharply varies.

With a recent development in miniaturization of semiconductor devices, the size of an opening 1a in resist 1 on wafer 3 shown in FIG. 8, i.e. a width of an etching pattern, has been decreased to a sub-micron order. In addition, an opening ratio of the opening 1a to the entire area of wafer 3 has been remarkably decreased from about 10% in the prior art to 5% and further to 1% or less. The decrease in the opening ratio means a decrease in variation of emitted-light spectrum due to $CO_2$ gas in the above-described example of etching with $SiO_2$. Consequently, it is difficult to exactly detect the end point in the above-described measuring technique.

For example, Jpn. Pat. Appln. KOKAI Publication No. 5-62943 and Jpn. Pat. Appln. KOKAI Publication No. 7-321094 disclose prior-art techniques of removing a drift of whole plasma light and improving S/N of signal, thereby enhancing sensitivity of detection.

In order to fully obtain the advantage of such techniques, it is important how to efficiently introduce the plasma light within the chamber into the spectroscope.

These prior-art documents describe that the efficiency of convergence of light to the spectroscope is enhanced by using a converging lens. FIGS. 10A, 10B and 11 illustrate how to use the converging lens for enhancing the efficiency of light convergence. Suppose that plasma light produced in a narrow space (a plasma producing region) between the upper electrode 7a and lower electrode 7b is represented by a horizontally elongated planar light source 4 (i.e. by dimensions of cross section of the plasma producing region). An incidence slit of the spectroscope is denoted by numeral 5.

FIG. 10A shows a case where no converging lens is provided. A light beam covering an effective numeral aperture NA (NAm) of the spectroscopic element (e.g. a concave grating) of the spectroscope through one point of the incidence slit 5 has to be collected from all point light sources within a circle 4a indicated on the planar light source 4. However, if the width of the planar light source 4 (i.e. the distance between the electrodes) is increased more than necessary, such an increased width will adversely affect the plasma process. Thus, the width is limited. Consequently, the amount of light in areas within the circle 4a projecting up an down from the width of the planar light source 4 becomes deficient. On the other hand, FIG. 10B shows a case where a converging lens 6 is provided between the planar light source 4 and incidence slit 5. In this case, if the converging lens having a numerical aperture enough to cover the effective numeral aperture of the spectroscopic element and the converging lens is situated such that an image of the incidence slit 5 having a width h and a length S1 may fall within a predetermined light strip 4b, all points of the incidence slit can pass a light beam of a numerical aperture enough to the spectroscopic element and the efficiency of light convergence to the spectroscopic device can be enhanced. This technique, however, is not sufficient.

BRIEF SUMMARY OF THE INVENTION

The object of the present invention is to provide an end-point detector for a plasma etcher, which uses a converging lens capable of efficiently guiding plasma light produced within a chamber to a spectroscope.

Considering light convergence efficiency, in a detector using a converging lens, a plane light source is supposed to be a source of plasma light. An actual source of plasma light, however, produces light at various horizontal points between electrodes. Accordingly, the inventors of the present invention have recognized that there is a case where plasma light cannot efficiently be guided to the spectroscope, unless light emitted from all points (e.g. indicated by circles in black in FIG. 11) between the upper electrode 7a and lower electrode 7b, as shown in FIG. 11. In the present invention, this problem is solved as follows.

An end-point detector for a plasma etcher, according to an aspect of the present invention, comprises:

at least one converging lens for receiving strip-like plasma light produced between electrodes of the plasma etcher; and spectroscopic means, having a slit located at a substantial rear-side focal plane of the converging lens, for detecting an etching end time point from a time-based variation of spectrum light intensity of the plasma light which has been converged at the slit and has passed through the slit, wherein the converging lens has a pupil diameter of not greater than $$\phi = \frac{W + \sqrt{W^2 - 8hlNA_m}}{2}$$

where W is a width of a short side of the strip-like plasma light produced between the electrodes, 1 is a distance between an end of each electrode and a pupil face of the converging lens, NAm is a numerical aperture required by the spectroscopic means, and h is a width of a short side of the slit of the spectro-scopic means, and wherein the converging lens has a numerical aperture of not less than NAm.

In this context, the "substantial" rear-side focal plane of the converging lens refers to not only the rear-side focal plane of the converging lens but also a face having the same function as the rear-side focal plane, such as the emission face of an optical element such as an optical fiber having its input end face located at the rear-side focal plane.

Furthermore, in the end-point detector according to another aspect of the invention, even if there is no real number solution for the pupil diameter $\phi$ in the above equation, the converging lens has preferably a pupil diameter of not greater than $\phi = 8W1NAm/\{\pi(W+h)\}$ and has preferably a numerical aperature of not less than NAm.

As a result, since the converging lens with high efficiency can be obtained by the device in one aspect, the plasma light produced in the chamber can efficiently be introduced into the spectroscope.

According to another aspect, even if there is no real-number solution in the above equation due to peripheral conditions and no optimal solution for the converging lens is obtained, the converging lens meeting the condition for enhancing the convergence efficiency at least higher than in the case of using the converging lens can be selected.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinbefore.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a view for describing plasma light within a chamber according to a first embodiment of the invention;

FIGS. 3A to 3C are views for explaining the relationship between a parallel beam group forming plasma light in the first embodiment and the pupil size of the converging lens;

FIG. 8 shows the state of reaction within the chamber of the plasma etcher;

FIG. 9 shows a relationship between a reaction time and a spectrum intensity within the chamber of the plasma etcher;

FIGS. 10A and 10B are views for describing a converging lens for guiding plasma light within the chamber of the plasma etcher into a spectroscopic element; and FIG. 11 is a view for describing the converging lens for introducing the plasma light within the chamber of the plasma etcher into the spectroscopic element.

DETAILED DESCRIPTION OF THE INVENTION

Embodiments of the present invention will now be described with reference to the accompanying drawings.

(First Embodiment)

Figure 1:
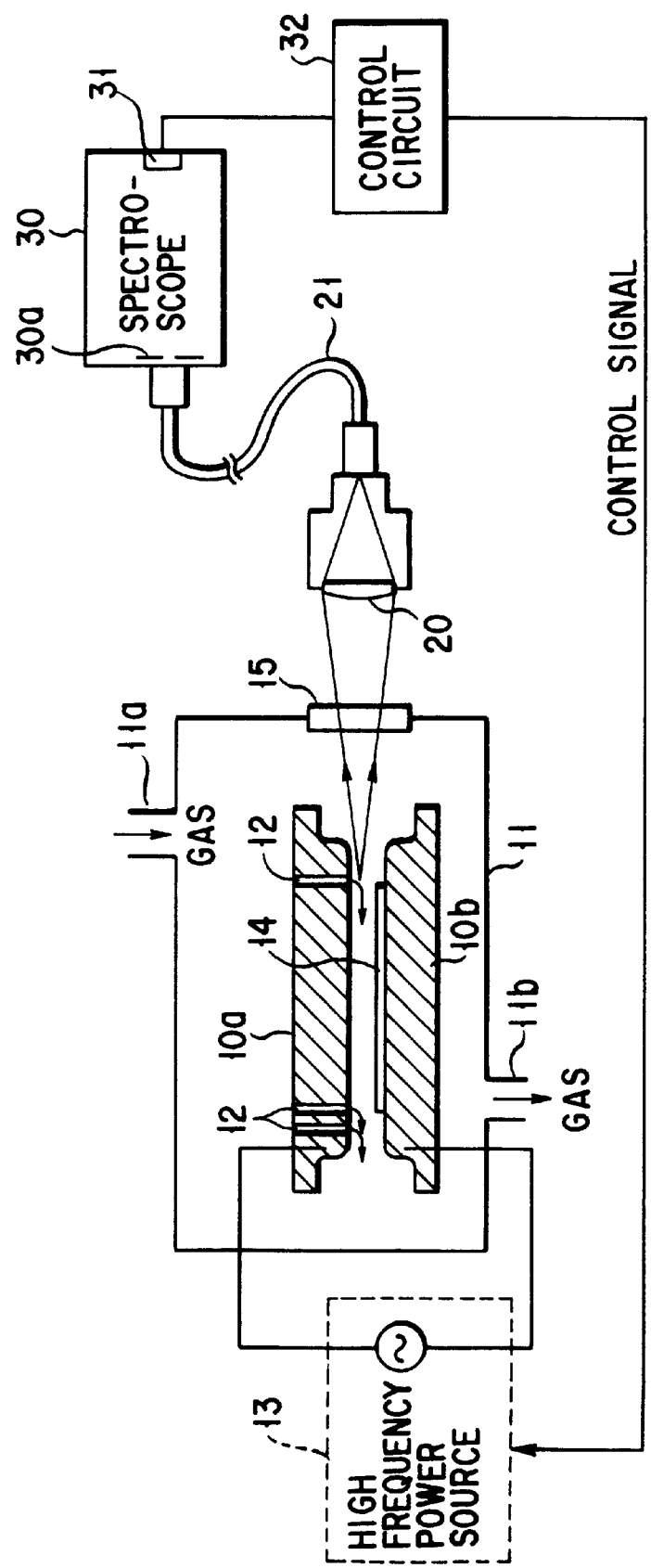
FIG. 1 schematically shows a general-type plasma etcher and an end-point detector according to an embodiment of the invention.

Referring to FIG. 1, the apparatus of the present invention will be described along with a plasma etcher to which the apparatus of this invention is applied.

The plasma etcher has a chamber 11 which is formed of a metal and hermetically sealed. An upper electrode 10a and a lower electrode 10b are arranged at a predetermined distance therebetween within the chamber 11. A radio-frequency voltage is applied to these electrodes from a radio-frequency power source 13. A number of fine holes 12 for passing a process or reaction gas are formed in the upper electrode 10a. The lower electrode 10b serves also as a susceptor having an upper surface on which a semiconductor wafer 14 or an object to-be-processed is placed. The mutually opposed surfaces of the upper and lower electrodes 10a and 10b are parallel at least at measuring-side end portions (to be described later). A top wall of the chamber 11 is provided with a gas introduction port 11a connected to a process gas source (not shown), e.g. a mixture gas source of, e.g. $CF_4$ and Ar. A bottom wall of the chamber 11 is provided with an exhaust port 11b connected to an exhaust apparatus (not shown). A process gas or an etching gas introduced into the chamber 11 from the introduction port 11a flows through the fine holes 12 in the upper electrode 10a into the space between the electrodes 10a and 10b, i.e. the plasma producing region, and the etching gas is made into a plasma. As a result, the semiconductor wafer (including an $SiO_2$ film, etc. formed on the wafer) placed on the lower electrode 10b is subjected to an etching process. During the etching process, the inside of the chamber 11 is exhausted through the exhaust port 11b and maintained at a predetermined vacuum level.

A view-port 15 of quartz glass is formed at a side wall of the chamber 11 so as to face the measuring-side end portions of the electrodes substantially on a level with the plasma producing region. A converging lens 20 provided outside the chamber 11 so as to face the view-port 15. The converging lens 20 collects plasma light from the plasma producing region through the view-port 15. An optical fiber 21 is provided behind the converging lens 20 such that an incidence face of the fiber 21 is situated in a rear focal plane of the lens 20. A spectroscope 30 and a photodetector 31 are connected in succession in a rear stage of the optical fiber 21 such that an incidence slit 30a is positioned at a light emission face of the fiber 21. The plasma light collected by the converging lens 20 is thus guided to the spectroscope 30 through the optical fiber 21 and slit 30a. In the spectroscope 30, a spectrum of the plasma light is obtained using a predetermined substance ($CO_2$ gas in this case). The photodetector 31 measures the spectrum intensity. The measurement is continued preferably throughout the plasma process. A control circuit 32 for controlling the radio-frequency power supply 13 is connected to the output side of the photodetector 31. The power source 13 is controlled by the control circuit 32 in accordance with the detected result of the photodetector 31. For example, the radio-frequency power supply 13 is turned off by the control circuit 32 when the photodetector 31 has detected the etching end region as described with reference to FIG. 9.

In the above structure, suppose that a distance W is set between the electrodes 10a and 10b within the chamber and strip-like plasma light is leaking from the region of distance W between the electrodes 10a and 10b, as shown in FIG. 2. In this case, it is considered, irrespective of a light path in a narrow space between the electrodes 10a and 10b, that the leaking plasma light is a parallel light beam group G comprising parallel beams #1 to #n each having width W. For example, suppose that each of the parallel beams of the parallel beam group G has adequate width and angle. In a case where the same area $\phi$ is illuminated with use of two lenses having pupil diameters $\phi$ and $\phi/2$ and an equal numerical aperture, the area $\phi$ is illuminated, in the case of FIG. 3A, by collecting parallel beams with area $\pi\phi^2/4$ at an angle $\theta$. On the other hand, in FIG. 3B, the area $\phi$ is illuminated by collecting parallel beams with area $\pi\phi^2/16$ at an angle $2\theta$. Although the area of the parallel beam in FIG. 3B is ¼ of that in FIG. 3A, the luminous flux density is four times higher since the angle is two times greater. Thus, the area $\phi$ can be illuminated with exactly the same luminance in FIGS. 3A and 3B.

It is thus found that in order to converge at maximum efficiency the parallel beam group G with width W from the region between the electrodes 10a and 10b through the converging lens 20 to the incidence slit 30a (or end face of optical fiber 21) corresponding to the area $\phi$, the following condition must be satisfied. That is, each light beam of the parallel beam group G necessary for illuminating the area corresponding to the width of the incidence slit 32 (or the core diameter of optical fiber 21) should always cover the pupil diameter of the converging lens 20. Inversely speaking, if the parallel beam group G from the region between the electrodes 10a and 10b does not meet the pupil plane of the converging lens 20, as shown in FIG. 3C, the area not met by the parallel beam group G becomes a light amount loss, resulting in a decrease in light convergence efficiency.

In the above description, only the numerical aperture in the vertical direction of the parallel beams from the region of distance W between the electrodes 10a and 10b is taken into account. The reason is that the plasma light from the chamber 11 has a horizontally elongated strip-like shape, as viewed in the direction of observation and it has a length and a light emission angle in the horizontal direction enough to obtain a sufficient numerical aperture.

The diameter $\phi$ of the converging lens 20 for maintaining the maximum efficiency is obtained in the following manner.

Figure 4:
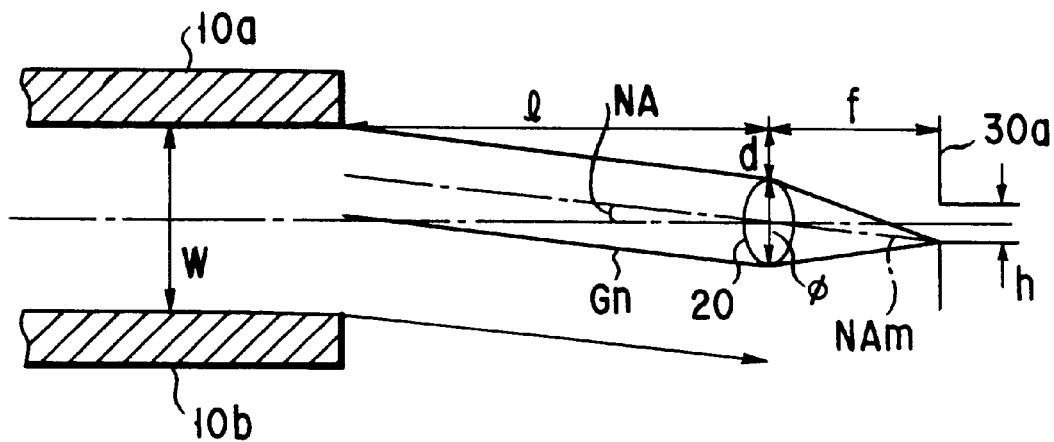
FIG. 4 is a view for explaining how to find the pupil size of the converging lens according to the first embodiment.
Figure 5:
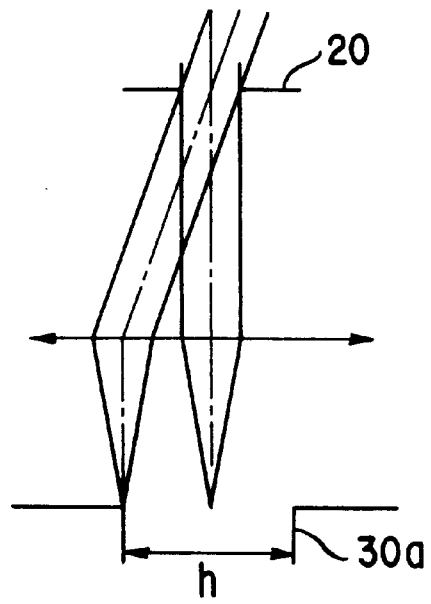
FIG. 5 is a view for describing a modification of the first embodiment.

In this case, as shown in FIG. 4, suppose that the dimension (width) of the short side of the strip-like plasma light from the region between the electrodes 10a and 10b is W, the distance from the end of electrode to the pupil face of the converging lens 20 is 1, an inclination or a numerical aperture of a light beam Bn of the parallel beam group G converging at the outermost end of the incidence slit 30a with height h is NA, and a rear-side focal distance of the converging lens 20 is f. In this case, the numerical aperture is h/2f. An allowance d of the converging lens 20 with diameter or pupil diameter $\phi$, which is located at distance 1 from one end of the light source (i.e. end of electrode) with width W (i.e. distance between the electrodes 10a and 10b), with respect to the width W between the electrodes 10a and 10b, is expressed by d=h1/(2f). Thus, a maximum allowance value of $\phi$ is given by $$\phi = W - 2d = W - (h1/f) \tag{1}$$

If the numerical aperture required by the spectroscope 30 is NAm, $$\phi/(2f) = NAm, \text{ and } f = \phi/(2NAm) \tag{2}$$

From equations (1) and (2), the pupil diameter $\phi$ of the converging lens 20 is given by $$\phi = \frac{W + \sqrt{W^2 - 8hlNA_m}}{2} \tag{3}$$

As a result, if W=5 mm, 1=80 mm, h=0.25 mm and NAm=0.15, for example, the pupil diameter $\phi$ of the converging lens 20 is 3 mm from equation (3).

It is accordingly possible to set the converging lens 20 having the pupil diameter of maximum allowance value $\phi$ or less obtained by equation (3) and having a numerical aperture of not less than NAm. Thereby, the converging lens 20 with maximum efficiency can always be obtained, and the plasma light produced within the chamber 11 can be efficiently introduced into the spectoscope 30 in a high density. Therefore, the etching end point can be exactly controlled in a high sensitive. It is easily understood by persons killed in the art that the minimum allowance value of pupil diameter and maximum numerical aperture may be set within ranges within which the advantages of the invention can be substantially obtained.

In fact, in order to optimally guide light into the slit 30a of spectroscope 30 having a width h of about 0.25 mm, as mentioned above, but having a great length of 7 to 8 mm, it should suffice to use a lens having a sufficient field of view in the longitudinal direction of the slit while having the above-mentioned value $\phi$. Although the actual diameter of such a lens may be considerably great, it will not impossible to design it.

Figure 6:
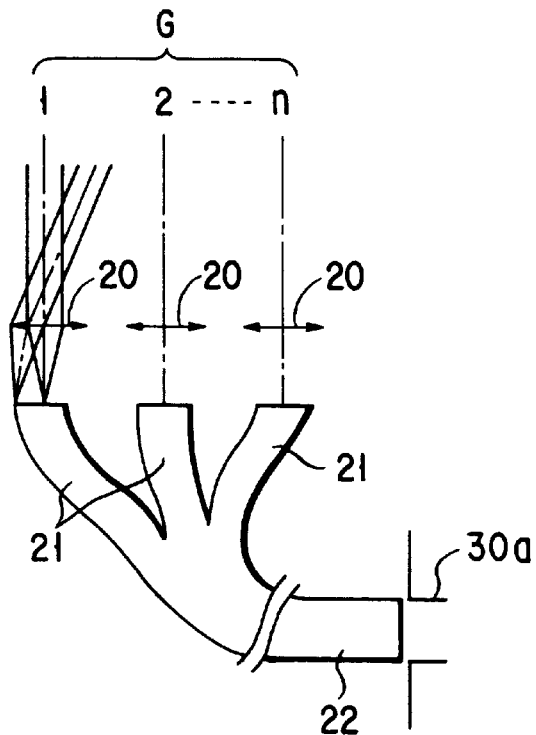
FIG. 6 is a view for describing another modification of the first embodiment.

In addition, a structure shown in FIG. 6 may be adopted. A plurality of converging lenses 20 each having a relatively small diameter of field of view are juxtaposed with respect to the parallel beam group G. Optical fibers 21 are arranged such that their incidence faces are located at rear-side focal planes of the converging lenses 20. These fibers are bundled into a single fiber bundle 22. A light emission face of the bundle 22 is situated on the slit 30a of spectroscope 30.

(Second Embodiment)

In the first embodiment, the optimal pupil diameter or effective shape of the converging lens 20 is set at 3 mm as a specific example. If the numerical aperture (NAm) required for the spectroscope 30 is set at 0.2, the value within the root in equation (3) becomes negative and there would not be no read number solution. In other words, if the aforementioned converging lens 20 of φ=3 mm is used as it is, the pupil of the converging lens 20 falls outside the parallel beam incident on an area near the outermost end of the slit 30a of spectroscope 30. As a result, the amount of incident light decreases.

The second embodiment aims at providing a converging lens 20 satisfying the conditions for enhancing the convergence efficiency, at least higher than in the case where the converging lens 20 is not used, even in the case where an optimal solution for the converging lens 20 cannot be obtained from equation (3) due to the above-mentioned causes.

Figure 7:
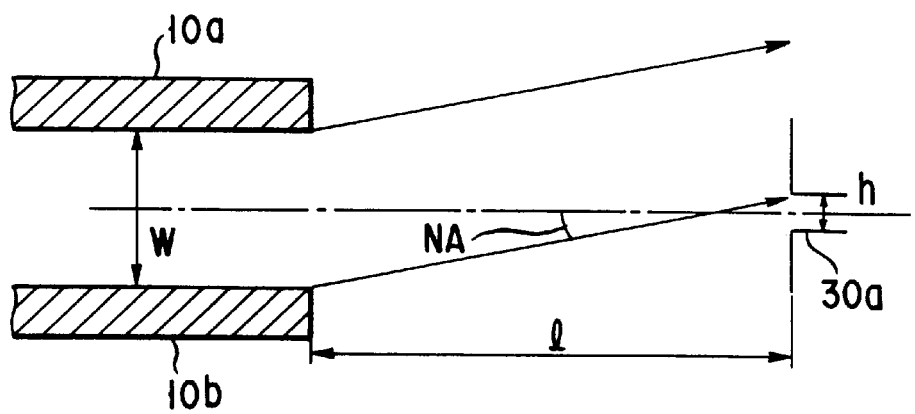
FIG. 7 is a view for describing a second embodiment of the invention.

In FIG. 7, if the converging lens 20 is not provided, a maximum inclination NA of the parallel beam with width W radiated on the incidence slit 30a with width h is expressed by $$(W+h)/(2l) \quad (4)$$

If the numerical aperture required by the spectroscope 30 is NAm, the ratio of the amount of light to the amount of light of the optimal converging lens (incident on all points at NAm) is given by $$(W+h)/(2lNAm) \quad (5)$$

On the other hand, from FIG. 3C, the ratio of the amount of light to the optimal light amount in a case where the pupil diameter of converging lens 20 is greater than W is expressed, as a ratio of the area of the pupil of converging lens 20 to the hatched area S, as follows:

$$\phi W/\{(\phi/2)^2 \pi\} \quad (6)$$

Thus, if equations (5) and (6) are supposed to be equal, the minimum effective diameter φ=0 is given by $$\phi = 8WlNAm/\{\pi(W+h)\} \quad (7)$$

In the meantime, if W=5 mm, l =80 mm, h=0.25 mm and NAm=0.2, it is found, from equation (7), that the effective diameter φ of converging lens 20 is 38.8 mm. Accordingly, even if there is no real number solution in equation (3) due to peripheral conditions and the optimal solution for the converging lens 20 cannot be found, the converging lens 20 having the pupil diameter of not greater than φ obtained by equation (7) and having the numerical aperture of not less than NAm may be obtained. Thereby, the converging lens 20 satisfying the conditions for enhancing the convergence efficiency, at least higher than in the case where the converging lens 20 is not used, can be suitably chosen.

As has been described above, according to the present invention, since the converging lens with maximum efficiency can be obtained, it is possible to efficiently guide plasma light within the chamber to the spectroscope and to precisely control the etching end time point.

Furthermore, even in a case where the converging lens with maximum efficiency cannot be obtained due to peripheral conditions, etc., it is possible to suitably choose the converging lens which ensures minimum improvement of efficiency.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:

1. An end-point detector for a plasma etcher, the detector comprising:

at least one converging lens for receiving strip-like plasma light produced between electrodes of the plasma etcher; and spectroscopic means, having a slit located at a rear-side focal plane of the converging lens, for detecting an etching end time point from a time-based variation of spectrum light intensity of the plasma light which has been converged at the slit and has passed through the slit, wherein said converging lens has a pupil diameter of not greater than $$\phi = \frac{W + \sqrt{W^2 - 8hlNA_m}}{2}$$

where W is a width of a short side of the strip-like plasma light produced between the electrodes, 1 is a distance between an end of each electrode and a pupil face of the converging lens, NAm is a numerical aperture required by the spectroscopic means, and h is a width of a short side of the slit of the spectro-scopic means, and wherein the converging lens has a numerical aperture of not less than NAm.

2. The end point detector according to claim 1, wherein even if there is no real number solution for the pupil diameter φ in the equation in claim 1, the converging lens has a pupil diameter of not greater than $$\phi = 8WlNAm/\{\pi(W+h)\}$$

and has a numerical aperture of not less than NAm.

3. The end-point detector according to claim 1, further comprising an optical fiber having a light incidence face located at the rear-side focal plane of the converging lens and having a light emission face located at the slit.

4. The end-point detector according to claim 1, further comprising:

a plurality of converging lenses arranged to receive the plasma light produced between the electrodes of the plasma etcher; and an optical fiber bundle comprising a plurality of optical fibers each having a light incidence face located at a rear-side focal plane of an associated one of the converging lenses, the optical fiber bundle having a light emission face located at the slit.

5. An end-point detector for a plasma etcher, the detector comprising:

at least one converging lens for receiving strip- like plasma light produced between electrodes of the plasma etcher; and spectroscopic means, having a slit located at a substantial rear-side focal plane of the converging lens, for detecting an etching end time point from a time-based variation of spectrum light intensity of the plasma light which has been converged at the slit and has passed through the slit, wherein said converging lens has a pupil diameter φ defined by $$\phi = \frac{W + \sqrt{W^2 - 8hlNA_m}}{2}$$

where W is a width of a short side of the strip-like plasma light produced between the electrodes, 1 is a distance between an end of each electrode and a pupil face of the converging lens, NAm is a numerical aperture required by the spectroscopic means, and h is a width of a short side of the slit of the spectroscopic means.

6. The-end point detector according to claim 5, wherein even if there is no real number solution for the pupil diameter φ in the equation in claim 1, the converging lens has a pupil diameter defined by φ=8W1NAm/{π(W+h)}.

7. The-end point detector according to claim 5, wherein the converging lens has a numerical aperture of not less than NAm.

* * * * *